(12) United States Patent
Bodony et al.

(10) Patent No.: US 8,849,015 B2
(45) Date of Patent: Sep. 30, 2014

(54) SYSTEM AND APPARATUS FOR HAPTICALLY ENABLED THREE-DIMENSIONAL SCANNING

(75) Inventors: Larry Bodony, Lexington, MA (US); Dan Cookson, Rowley, MA (US); Curt Rawley, Windham, NH (US); David Tzu-Wei Chen, Wrentham, MA (US)

(73) Assignee: 3D Systems, Inc., Rock Hill, SC (US)

( * ) Notice: Subject to any disclaimer, the term of this patent is extended or adjusted under 35 U.S.C. 154(b) by 190 days.

(21) Appl. No.: 13/271,759

(22) Filed: Oct. 12, 2011

(65) Prior Publication Data
US 2012/0141949 A1 Jun. 7, 2012

Related U.S. Application Data

(60) Provisional application No. 61/392,418, filed on Oct. 12, 2010, provisional application No. 61/426,729, filed on Dec. 23, 2010.

(51) Int. Cl.
*G06K 9/00* (2006.01)
*A61C 9/00* (2006.01)
*G01B 11/25* (2006.01)

(52) U.S. Cl.
CPC .............. *A61C 9/0053* (2013.01); *G01B 11/25* (2013.01)
USPC ............... 382/154; 700/98; 700/245; 700/65; 700/83; 700/85; 600/427; 600/102; 600/109

(58) Field of Classification Search
CPC . G06K 9/00201; G06K 9/62; H04N 13/0221; G06T 15/00; G06T 1/0007; G06T 15/08; G06T 7/0012; G06F 3/016
USPC .................. 382/154; 700/98, 245, 65, 83, 85; 600/427, 102, 109
See application file for complete search history.

(56) References Cited

U.S. PATENT DOCUMENTS

| | | | |
|---|---|---|---|
| 5,898,599 A | 4/1999 | Massie et al. | |
| 6,111,577 A | 8/2000 | Zilles et al. | |
| 6,421,048 B1 | 7/2002 | Shih et al. | |
| 6,671,651 B2 | 12/2003 | Goodwin et al. | |
| 6,867,770 B2 | 3/2005 | Payne | |
| 6,958,752 B2 | 10/2005 | Jennings, Jr. et al. | |
| 6,985,133 B1 | 1/2006 | Rodomista et al. | |
| 7,149,596 B2 | 12/2006 | Berger et al. | |
| 7,411,576 B2 | 8/2008 | Massie et al. | |
| 7,626,589 B2 | 12/2009 | Berger | |
| 7,990,374 B2 | 8/2011 | Itkowitz et al. | |
| 8,040,345 B2 | 10/2011 | Faken et al. | |
| 8,359,114 B2 | 1/2013 | Steingart et al. | |
| 2006/0284834 A1 | 12/2006 | Itkowitz et al. | |
| 2007/0038080 A1* | 2/2007 | Salisbury et al. | 600/427 |
| 2008/0246761 A1 | 10/2008 | Faken et al. | |
| 2008/0261165 A1* | 10/2008 | Steingart et al. | 433/24 |
| 2009/0149977 A1* | 6/2009 | Schendel | 700/98 |
| 2009/0248184 A1 | 10/2009 | Steingart et al. | |
| 2010/0291505 A1 | 11/2010 | Rawley et al. | |

* cited by examiner

*Primary Examiner* — Mike Rahmjoo

(57) ABSTRACT

Described herein is a three-dimensional scanning system that features a camera integrated with a user-guided haptic interface device. The system allows an operator, through the sense of touch, to intuitively and interactively identify optimum locations for obtaining images or scans of an object. The system then assembles these scans to produce a virtual three-dimensional representation of the object with a high degree of accuracy and with a minimum of data artifacts.

19 Claims, 6 Drawing Sheets

SYSTEM AND APPARATUS FOR HAPTICALLY ENABLED THREE-DIMENSIONAL SCANNING

CROSS-REFERENCE TO RELATED APPLICATIONS

This patent application claims the benefit of U.S. Provisional Patent Application No. 61/392,418, filed on Oct. 12, 2010, and U.S. Provisional Patent Application No. 61/426,729, filed on Dec. 23, 2010, the disclosures of which are hereby incorporated by reference herein in their entireties.

FIELD OF THE INVENTION

This invention relates generally to scanning systems for constructing three-dimensional models of objects. More particularly, in certain embodiments, the invention relates to a scanning system that includes a scanning module integrated within a user-guided haptic interface device.

BACKGROUND OF THE INVENTION

A common requirement for Dental CAD/CAM systems is the acquisition of a true three-dimensional representation of the patient situation—that is, the shape of the patient's existing teeth, gums and palette—with the appropriate degree of accuracy for the prosthetic that is to be designed. Three-dimensional scanning systems sold to dental labs most often digitize the "stone" model, made by plaster casting the patient impression made by the dentist. In some cases, the patient impression is digitized directly. Three-dimensional scanning systems sold directly to dentists often employ "intra-oral scanning" techniques where the digitizer is inserted directly into the patient's mouth.

Different range sensing techniques have been used to engineer dental lab scanners and intra-oral scanners, including: triangulation, phase-shift reconstruction, conoscopic holography, confocal microscopy, and time of flight. Most commercial dental lab scanners use triangulation and phase-shift reconstruction. These both work through projecting structured light onto the object to be digitized, capturing an image (or images) with a frame grabber, and then reconstructing the image on the computer to produce Point Cloud (X, Y, Z) data relative to the point of view of the image capture device(s).

Conoscopic holography is based on crystal optics and interference patterns generated by interacting polarized light rays. The NOBEL BIOCARE™ dental lab scanner uses this technique.

Confocal microscopy uses an image capture system with a very narrow field of focus and then varies the focal plane in a known sequence. Several intra-oral scanners, such as the ITERO™ by CADENT™, use the confocal principle to construct Point Cloud data.

Time of flight systems direct light (usually from a laser source) against an object and measure the amount of time to detect the reflection. Since the speed of light c is constant, the distance to the object may be calculated. Because the precision of the time measurement is limited, and the accuracy requirements for dental scanners is relatively high (in the range of 10-30 microns), time of flight has not yet been used for dental scanners.

Three-dimensional scanning is largely done with hardware and software that is dedicated to scanning, rather than with general purpose hardware and software. Three-dimensional scanning devices are generally classified according to the underlying technology, such as white light, non-white light, point, line, and phase change. Three-dimensional scanning devices may operate in one of three modes: fully automatic, semi-automatic, and manual.

One of the central problems in capturing scan data for analysis in creating a three-dimensional model is that of controlling camera position and orientation relative to the object being scanned. Given a fixed camera focal length based on the lens configuration, if the camera is at the optimal focal distance from the object, then mathematically precise scan data may be extracted from the images. By combining a sufficient number of such images, and by knowing the position of the object and the camera locations and orientations from which the images were collected, a high quality three-dimensional reconstruction may be created. Failing to control camera position and orientation, however, may lead to ambiguity in the collected data, thereby rendering the three-dimensional reconstruction an approximation with unknown accuracy.

There is a need for improved methods, systems, and apparatus for scanning an object to produce a virtual three-dimensional representation of the object.

SUMMARY OF THE INVENTION

Described herein is a three-dimensional scanning system that features a camera integrated with a user-guided haptic interface device. The system allows an operator, through the sense of touch, to intuitively and interactively identify optimum locations for obtaining images or scans of an object. The system then assembles these scans to produce a virtual three-dimensional representation of the object with a high degree of accuracy and with a minimum of data artifacts. In the dental field, for example, the object being scanned may be the interior of a patient's mouth (or an impression or cast thereof, such as a dental stone), and the haptic interface device may include a stylus with a camera at the end. The three-dimensional representation of the scanned object may be used, for example, for preparation of dentures, crowns, dental appliances, implants, or other dental devices, custom fitted for the patient.

One or more haptic guides facilitates acquisition of useful images of the object by the user. For example, the movement of a haptic interface device being manipulated by a user about the object being scanned may be constrained to (and/or may "snap to") a particular 2D or 3D surface, region, line, point, and/or orientation in space in relation to the object being scanned, in order to guide the user to obtain useful data for construction of the virtual 3D representation of the object. In the example given above, the haptic guide(s) would constrain (either strongly or weakly) the movement of the stylus to camera locations and orientations from which useful images may be obtained. The user may acquire images at such locations, for example, by pressing a button on the haptic interface device. As the user obtains more images, the haptic guide(s) may be updated based on the newly acquired images. By acquiring three-dimensional data in real-time, the haptically guided scanning system allows the operator to easily identify and interactively fill in voids of the constructed virtual representation (model). By watching the model being filled-in on a display monitor in real-time, and by sensing in real-time the haptic guides that direct the user to optimum data acquisition locations, the operator feels as if he is "crayoning" the object being scanned to make the three-dimensional details emerge on the screen.

This intuitive, manually guided scanning system is faster than automated scanning processes and provides better, more accurate resolution of surfaces, particularly for objects having high curvature, undercuts, and/or deep or discontinuous regions, such as gaps between teeth and/or impressions, for example. Because of the crayoning effect experienced by the user, the user may interactively scan until the model is completely filled-in, so that there is little or no need for post-acquisition hole filling or other artifact removal. In certain embodiments, the system may be used to scan regions (e.g., interior regions of the body) for which adequately detailed impressions cannot be readily obtained. For example, three-dimensional representations of thusly scanned regions may be used for production of custom joints, prostheses, and/or other medical appliances.

Besides the application of scanning dental stones, the technology described herein is generally applicable to other dental, medical, or reverse engineering scanning tasks. In certain embodiments, the invention provides systems and methods for real-time image reconstruction, thereby enabling use of the Haptic Scanner to create 3D point clouds for moving or soft tissues.

In the dental field, the Haptic Scanner described herein can be used, for example, for intra-oral scanning, wherein the dentist directly images the patient's teeth (and mouth interior) without creating the intermediate impression or stone. In this case, the haptic device may include an extension joint so that the camera and projector scanner combination can be inserted into the mouth and access the distal areas where the molar teeth are positioned.

By using a larger haptic device, such as PHANTOM® Premium 3.0, manufactured by SensAble Technologies, Inc. of Wilmington, Mass., it is possible to use the haptic scanner to acquire 3D data of a person's face. This is useful in dentistry, for example, to measure "eye to smile" parameters that are used when a patient needs full dentures; in cranial-maxilla facial surgery planning; or as an input for a facial recognition security application, for example.

A larger haptic device also enables three-dimensional scanning for orthotics and prosthetics applications. For example, the shape of a patient's residual limb can be digitized as part of the process for making an artificial arm or leg. The haptic device may also be used to scan the shape of the head for cranial helmets, the shape of the foot for custom orthotics, and the overall shape of the torso to create custom back braces.

The haptic device can also be arranged in a typical "master/slave" configuration where the haptic scanner is attached to a slave device that is controlled through a haptic master such as the PHANTOM® DESKTOP™ or PHANTOM® OMNI®, manufactured by SensAble Technologies, Inc. This configuration can be more convenient for the user in many situations where the object to be scanned is either very large, very small, or otherwise only remotely accessible to the user; but the fundamental "crayoning" interface should remain intact.

On a commercial scale, scanning for reverse engineering is one of the largest application areas, and the haptic scanner is well suited to this application as well. Engineering parts or shapes may contain many concave or "hidden" features where the flexibility provided by the invention's haptically guided scanning capability will provide an easy and intuitive user interface. In one embodiment, the scanning system is used to create a three-dimensional virtual model of an existing physical part for use in 3D CAD, CAM, CAE or other software. The virtual model may be used, for example, to analyze how a product works, how much it costs, what it consists of, and/or to identify potential patent infringement.

In one aspect, the invention is directed to a system for haptically enabled, three-dimensional scanning of an object, the system comprising: a haptic interface device configured to provide haptic feedback to a user and receive input from the user during movement of an implement (e.g., a stylus) of the haptic interface device during three-dimensional scanning of an object, wherein the implement comprises a camera; a graphical interface configured to provide graphical feedback to the user during three-dimensional scanning of the object; and a three-dimensional scanning application in communication with the haptic interface device and the graphical interface, wherein the scanning application is configured to: (a) obtain an image of the object upon activation of a user command (e.g., upon the pressing of a button of the haptic interface device by the user); (b) determine a haptic guide at one or more positions and/or orientations in space in relation to the object from which advantageous acquisition of images is possible for construction of a three-dimensional virtual representation of the object, wherein the haptic guide is determined using at least the image obtained in step (a); (c) deliver force to the user via the haptic interface device according to the haptic guide (e.g., constrain the movement of the implement by the user to the advantageous positions and/or orientations corresponding to the haptic guide); (d) repeat one or more of steps (a) to (c) as additional images of the object are acquired; and (e) produce a three-dimensional virtual representation of the object using at least a subset of the images obtained. In certain embodiments, the three dimensional scanning application comprises a memory that stores code defining a set of instructions and a processor that executes the instructions. In one embodiment, the system is configured for use in a minimally invasive surgery (MIS) system.

In another aspect, the invention is directed to a method for haptically enabled, three-dimensional scanning of an object, the method comprising: (a) obtaining an image of the object upon activation of a user command (e.g., upon the pressing of a button of the haptic interface device by the user), wherein the image is obtained during manipulation by the user of an implement (e.g., stylus) of a haptic interface device about the object; (b) delivering graphical feedback to the user via a graphical display during the manipulation of the implement of the haptic interface device by the user; (c) determining a haptic guide at one or more positions and/or orientations in space in relation to the object from which advantageous acquisition of images is possible for construction of a three-dimensional virtual representation of the object, wherein the haptic guide is determined using at least the image obtained in step (a); (d) delivering a force to the user via the haptic interface device according to the haptic guide (e.g., constraining the movement of the implement by the user to the advantageous positions and/or orientations corresponding to the haptic guide); (e) repeating one or more of steps (a) to (d) as additional images of the object are acquired; and (f) producing a three-dimensional virtual representation of the object using at least a subset of the images obtained. The description of elements of the embodiments above can be applied to this aspect of the invention as well.

In certain embodiments, the object is a tooth, a human face, a residual limb, an anatomical structure (e.g., an organ), or a mechanical part. The method may also include analyzing the three-dimensional virtual representation to reverse engineer the object.

In yet another aspect, the invention relates to an apparatus for scanning an object. The apparatus includes a user connection element, a scanning module associated with the user connection element, an actuator, a linkage physically linking the user connection element to the actuator, and a processor for determining force delivered to the user connection element by the actuator to restrict or guide movement of the user connection element according to a haptic guide. The scanning module acquires a plurality of images of the object during the scan. The description of elements of the embodiments above can be applied to this aspect of the invention as well.

In certain embodiments, the user connection element includes an extension joint for scanning a difficult to reach object, which may include a tooth, a human face, a residual limb, an anatomical structure, and/or a mechanical part. The haptic guide may be configured to facilitate movement of the user connection element by the user to one or more positions and/or orientations in space in relation to the object from which advantageous acquisition of images is possible for construction of a three-dimensional virtual representation of the object from the acquired images. The haptic guide may be updated according to one or more previously obtained images of the object. In certain embodiments, the scanning module is configured for use in a minimally invasive surgery (MIS) system.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

While the invention is particularly shown and described herein with reference to specific examples and specific embodiments, it should be understood by those skilled in the art that various changes in form and detail may be made therein without departing from the spirit and scope of the invention.

DETAILED DESCRIPTION

Figure 1:
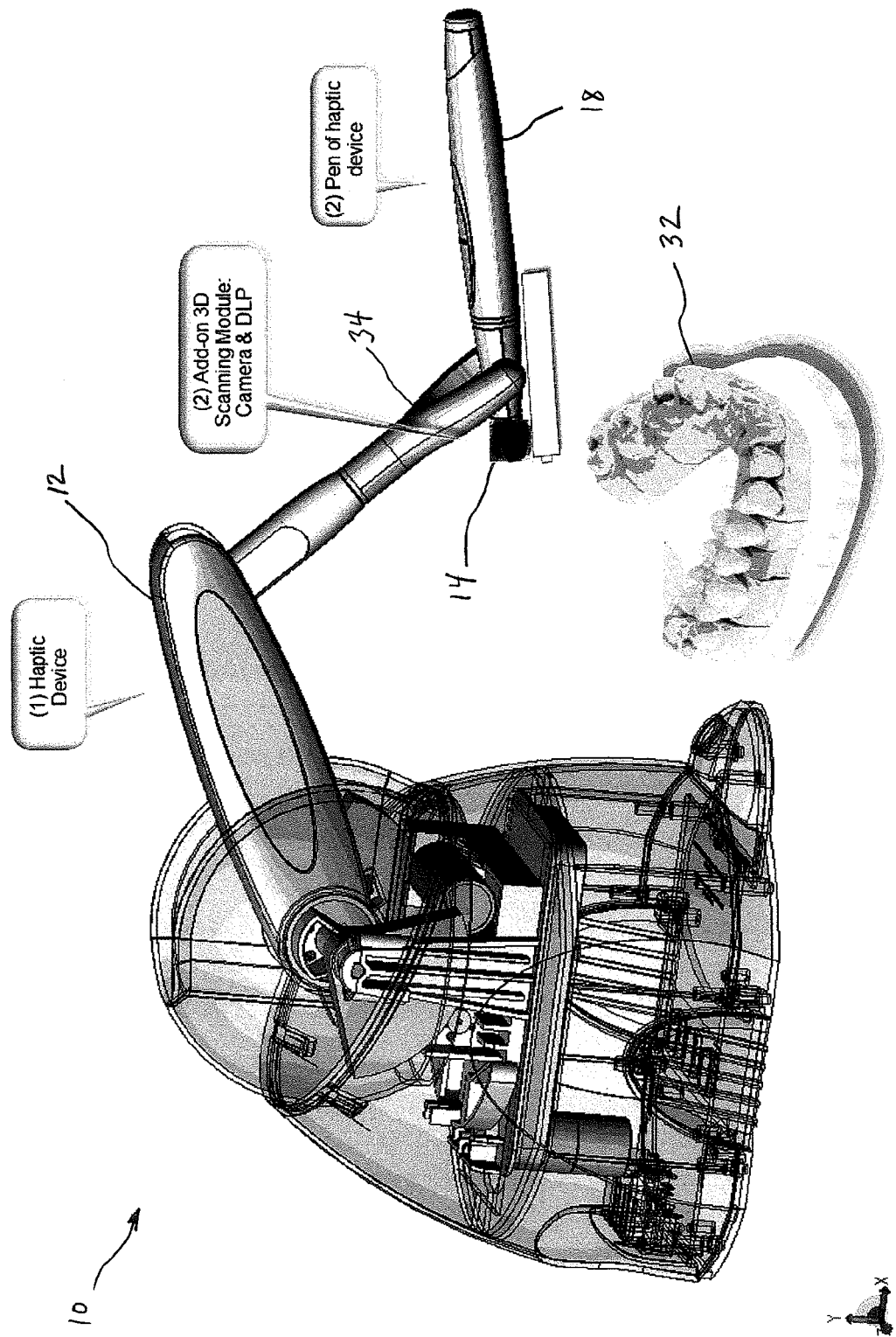
FIG. 1 is a schematic perspective view of a haptically guided scanning system, according to an illustrative embodiment of the invention.

It is contemplated that devices, apparatus, systems, methods, and processes of the claimed invention encompass variations and adaptations developed using information from the embodiments described herein. Adaptation and/or modification of the devices, apparatus, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

As discussed above, one of the central problems in capturing scan data for analysis in creating a three-dimensional model is that of controlling camera position and orientation relative to the object being scanned. Failing to control camera position and object position may lead to ambiguity in the collected data, thereby rendering the three-dimensional model an approximation with unknown accuracy.

The methods, systems, and apparatus described herein address these issues by enabling an operator to control camera position and orientation through the use of haptic guides. A haptic guide may be, for example, a constraint (e.g., weak or strong) that limits or guides a user's movement of an implement of the haptic interface device, e.g., a stylus, about the object being scanned. The haptic guide is "felt" by the user via force feedback delivered to the user as the user moves the implement of the haptic interface device. Examples of such constraints are "hotspots," gravity wells, and other haptic cues. The haptic guide may be, for example, a point constraint, line constraint, 2D or 3D surface constraint, and/or orientation constraint. Haptic detents are dents or bumps that are sensed by a user moving an implement of the haptic interface device in space in the vicinity of certain points in space. The haptic guide may provide a "snap-to" an advantageous position, line, or surface, for image/scan data acquisition. Such a haptic guide may have a "snap-distance" associated with the guide, whereby a user will sense, via force feedback delivered by the haptic interface device, a "force field" encouraging movement of the haptic interface device implement (e.g., stylus) to the advantageous position or orientation.

Images obtained from a current camera position are analyzed by any one of several methods, e.g., via structured light, to determine how the camera should be repositioned to improve the source data being captured. The result of this analysis is then transformed into haptic guidance to assist the operator in repositioning the camera to an improved location. This cycle of capturing, analyzing, and haptically guiding the camera to an improved location is repeated—for example, at hundreds of cycles per second—until the camera is guided to a position within a preferred tolerance of optimal location and/or orientation for image capture, and a single frame is captured to serve as one of several in the final set to be analyzed. This process is again repeated with the operator choosing a new vantage point to initialize each iteration and being guided haptically to an additional optimal location at which point another final image is collected. The image collection is repeated until a sufficient number of high quality images have been collected to enable a high quality three-dimensional reconstruction.

In one embodiment, to perform a scan, the object to be scanned is placed on a fixture or a simple surface. The operator then navigates a stylus which is part of a haptic interface device to positions in three-dimensional space along the haptic guide around the object. The haptic guide may act as a "force field" limiting motion of the stylus to positions and/or orientations from which useful optical/image data of the object being scanned may be obtained. Each time the operator determines that a camera position would be good for capture, images are captured and become part of the scan. The operator may then move to additional locations in space around the object to capture more images. The system may update the haptic guide as more images/data are obtained, modifying the haptic guide in light of the additional data obtained. The process continues until a sufficient number of images have been collected to enable high quality three-dimensional reconstruction of the three-dimensional object being scanned. The systems described herein may be used to scan many different types of objects, both large and small, such as bones, teeth, and tissue, and/or impressions or casts thereof. In addition, the systems may be used to scan objects that reside inside or outside of a patient's body, or wherever an operator may be haptically guided while scanning an object.

Figure 2:
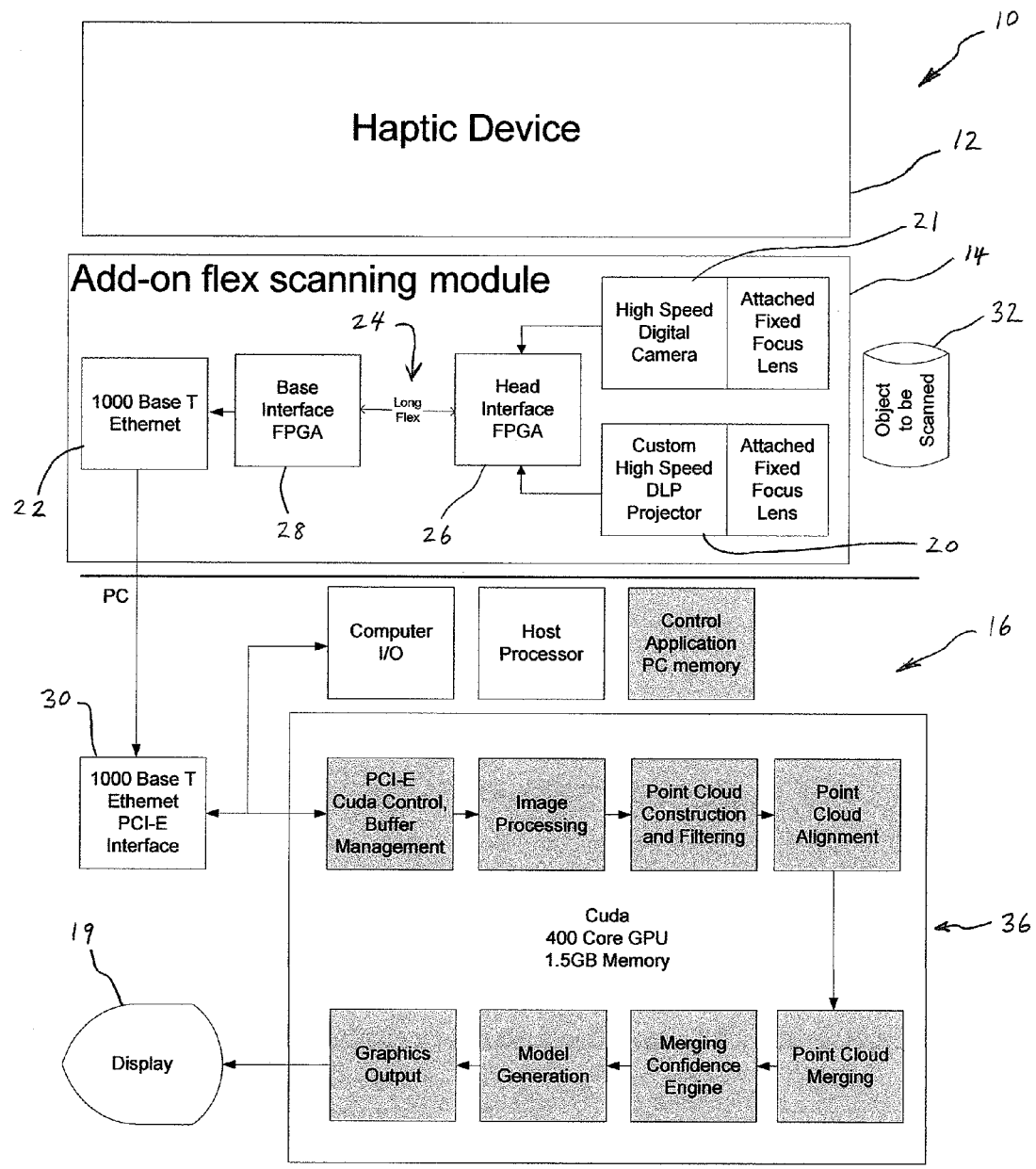
FIG. 2 is a flowchart depicting a haptically guided scanning system, according to an illustrative embodiment of the invention.

Referring to FIGS. 1 and 2, in one embodiment, a haptically guided scanning system 10 includes a haptic device 12, a three-dimensional scanning module 14, and a computer with haptic software 16. The haptic device 12 may be a three degree of freedom or six degree of freedom haptic device. In one embodiment, the haptic device 12 is the same as or similar to, for example, PHANTOM® OMNI® or DESKTOP™, manufactured by SensAble Technologies, Inc. The haptic device 12 includes a pen or stylus 18 that may be held and manipulated by an operator of the haptic device 12. Integrated into a tip or other portion of the stylus 18 is the three-dimensional scanning module 14. The computer with haptic software 16 receives scan data, such as image data, from the scanning module 14 and provides the operator with force feedback by guiding the movement of the stylus 18. Images from the scanning module 14 are displayed in a video window of a computer monitor 19 or other display device.

In the embodiment depicted in FIG. 2, the scanning module 14 includes a projector 20 or laser for projecting structured light, such as line patterns, and at least one camera 21 for viewing the structured light as it strikes an object. The projector 20 may be a custom high speed digital light projection (DLP) projector. In one embodiment, the projector 20 is in the form of an annular ring surrounding the camera lens. The light may include a mask for projecting structured light. The at least one camera 21 may be a high speed digital camera with an attached fixed focus lens, a high resolution CCD camera, and/or a three-dimensional range camera.

Although the scanning module 14 depicted in FIG. 2 uses triangulation based on projected line patterns, other scanning methods may be utilized, such as phase-shift reconstruction, conoscopic holography, confocal microscopy, and time of flight. In one embodiment, the scanning module 14 is a white light phase change scanner.

Referring to FIG. 2, data from the camera 21 is processed using one or more integrated circuits, such as field-programmable gate arrays (FPGAs), and transferred to the computer 16 using a 1000 Base T Ethernet connection 22. A flexible connection 24 is used to transfer data from a head interface FPGA 26 at a head of the haptic device 14 to a base interface FPGA 28 at a base of the haptic device 14. The computer 16 may include an expansion card 30, such as a PCI-E interface.

The computer and haptic software 16 are used to guide a manual scanning process in which an operator aims the scanning module 14 at an object 32 to be scanned. Specifically, the computer and software 16 guide the operator during the scan by providing force feedback through the stylus 18. This haptic guidance allows the operator to maintain the scanning module 14 at or near the proper orientation and optimal distance from the object 32. In one embodiment, the haptic device 12 includes an integrated extension that provides a reference frame for the scanning operations. The integrated extension may include fiducial marks.

Operation of the scanning system 10 begins during a setup phase when the object 32 is placed in front of the haptic device 12 (or on the integrated extension of the device), and the scanning application or software is started. Holding the stylus 18, the operator pulls an arm 34 of the haptic device 12 away from the object 32, out to its farthest position. With the scanning module 14 aimed at the object 32 (or at fiducial marks included on the integrated extension), the operator starts the scanning operation by pushing a stylus button. Images from the camera 21 are displayed on the computer monitor 19 and provide visual feedback to the operator during the scan. By viewing these images, the operator may see digitized images and a structured light fringe pattern projected from a DLP projector.

After the scanning process has been initiated, the operator moves the stylus 18 towards the object 32 until a haptic guide is felt. The haptic guide helps the user maintain the optimal distance and orientation between the camera 21, such as a three-dimensional range camera, and the object 32. At this point, the monitor 19 displays a small section of the digitized three-dimensional model and a corresponding haptic guidance surface.

Once the haptic guide has been contacted, the operator uses visual and force feedback to move the stylus 18 and scanning module 14 along the haptic guide to reveal a three-dimensional model or image of the object 32. As more points of the three-dimensional model are digitized, the haptic guide is updated and expanded accordingly. With this approach, the operator is free to focus efforts on digitizing and resolving areas or points of clinical significance. In addition, by avoiding features of the object 32 that do not need to be scanned and/or included in the three-dimensional model (e.g., regions that are not needed for creating a final prosthetic), subsequent trimming of the model may be unnecessary. Once the object 32 has been scanned as desired, the operator releases the stylus button to indicate that the scan is complete.

During the scanning process, scan data is acquired and analyzed to form Point Cloud data for the object 32, which may be any object, such as a bone, tissue, an organ (e.g., a gall bladder or a prostate gland), a tooth, or a dental stone. The Point Cloud data may be used both to interactively visualize a preliminary scan and to provide haptic guidance during the actual scan. For example, three-dimensional scanning systems generally have an ideal depth of field and range of focus within which the Point Cloud data will be most accurate. The haptic guidance allows the operator to enforce the ideal object to scanning module distance. Additionally, since the three-dimensional acquisition occurs in real time, haptic guides may be programmed to help the stylus 18 settle and/or to help the user hold the stylus 18 still during the data acquisition stage.

Because the haptically guided scanning system 10 is intended to acquire three-dimensional data in real-time, the operator may easily identify and fill voids in the captured model interactively. By watching the model fill-in interactively, the operator feels as if he is "crayoning" the object 32 to make the three-dimensional details emerge.

The scanning system 10 presented herein offers several advantages over other scanning systems used for similar purposes. For example, the system described herein provides an intuitive, manually guided scanning process that is faster than automated or semi-automated processes. The system also provides better, more accurate resolution of surfaces, particularly for objects 32 having high curvature and/or deep or discontinuous regions, such as gaps between teeth and/or impressions. Due to the crayoning aspect described above, the operator may interactively scan until the model is completely filled-in, so that there is little or no need for post-acquisition hole filling. In addition, the cost of the scanning hardware is low because it is based on a simple, short-focus optical system. The scanning system 10 also works with any computer capable of haptics. Finally, high quality scans may be obtained using existing three-dimensional scanning technologies, such as triangulation and/or structured light.

Referring to FIG. 2, in another aspect, the real-time performance of the image capture, display, filtering, and meshing is maximized through pipelining. An advantage of choosing three-dimensional scanner technology that is based on digital cameras and embedded projection, such as DLP by Texas Instruments, Inc., is that costs will naturally fall and the technology will be pushed ahead by the large consumer, digital video, and gaming markets. The systems described herein leverage these trends while maintaining real-time, three-dimensional performance by pipelining the data flow through a Graphics Processing Unit (GPU) 36, such as the NVIDIA® line of graphics cards. The NVIDIA® QUADRO® or GEFORCE® boards can be found commonly on graphics oriented workstations that are optimized for three-dimensional graphics or gaming.

The GPU architecture is well suited to address problems that may be expressed as "data-parallel" computations—where the same machine instructions are executed on many data elements all at once. This removes the typical CPU requirements for sophisticated flow control. Applications that process large data sets such as arrays may benefit from a data-parallel programming model. Three-dimensional rendering algorithms that process large numbers of pixels and vertices may also be mapped to parallel threads. Similarly, image processing algorithms, such as those used for video post-processing, image scaling, or pattern recognition, may also be accelerated by data-parallel processing.

Figure 3:
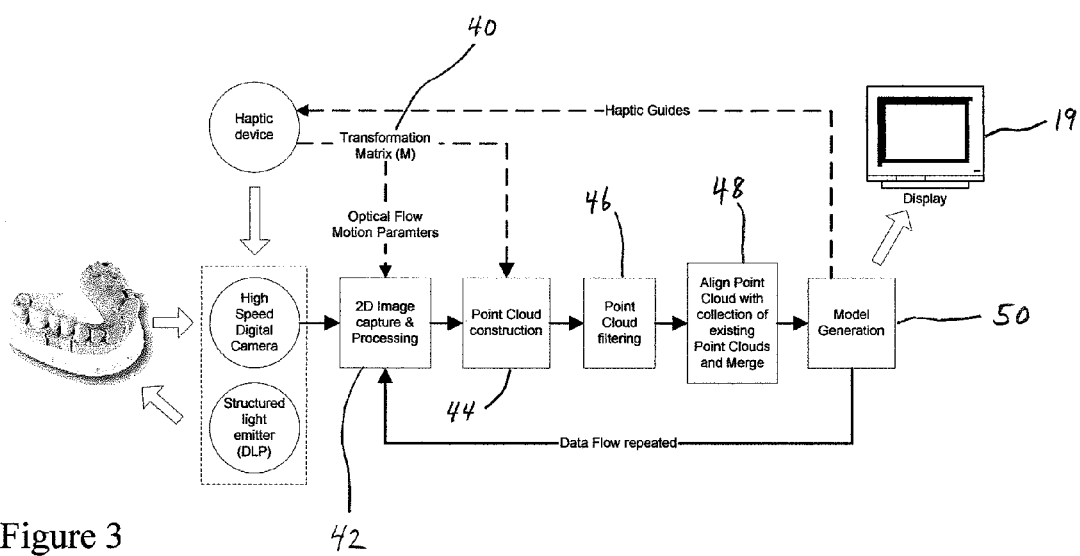
FIG. 3 is a flowchart depicting the data flow for a haptically guided scanning system, according to an illustrative embodiment of the invention.

FIG. 3 depicts the data flow for an embodiment that utilizes white-light triangulation. A transformation matrix M is derived (step 40) based on the x, y, z position and gimbal pitch, roll, and yaw of the stylus 18 of the haptic device 12. The scanning module 14 is used to capture structured light images of the object 32 being scanned. To correct image quality problems, such as optical distortion, or improper gain and/or contrast, two dimensional image processing is applied (step 42). An X, Y, Z Point Cloud is constructed (step 44) using triangulation, based on the captured images, and the transformation matrix M is applied. Next, the Point Cloud is filtered (step 46) based on local, regional information and current overall Point Cloud collection. The Point Cloud is then aligned with existing collection of Point Clouds (e.g., using an Iterated Closest Point ICP algorithm) and data is merged (step 48). During the merge step (step 48), a "confidence measure" for the Point Cloud points is generated. The model is then updated and displayed (step 50) on the computer monitor 19 for the operator, and the process is repeated until the operator is satisfied that all voids have been filled.

The data flow steps described above may not all be necessary and/or the data flow may include additional steps. For example, Point Cloud data may be thinned or merged to remove overlapping points. In addition, surfaces may be defined through triangulation or meshing of the Point Cloud collection. Mesh processing may include smoothing or decimation.

In one embodiment, a pipelined data flow is implemented through a series of data-parallel computations. Real-time, three-dimensional reconstruction is achieved by organizing each discrete function so that data, memory, and GPU cycles are always available. As with other pipelined systems, the time taken for processing the first series of captured frames will be the total time taken for each function, whereas the additional time to process successive frames is limited only by the latency of the slowest discrete function.

Figure 4:
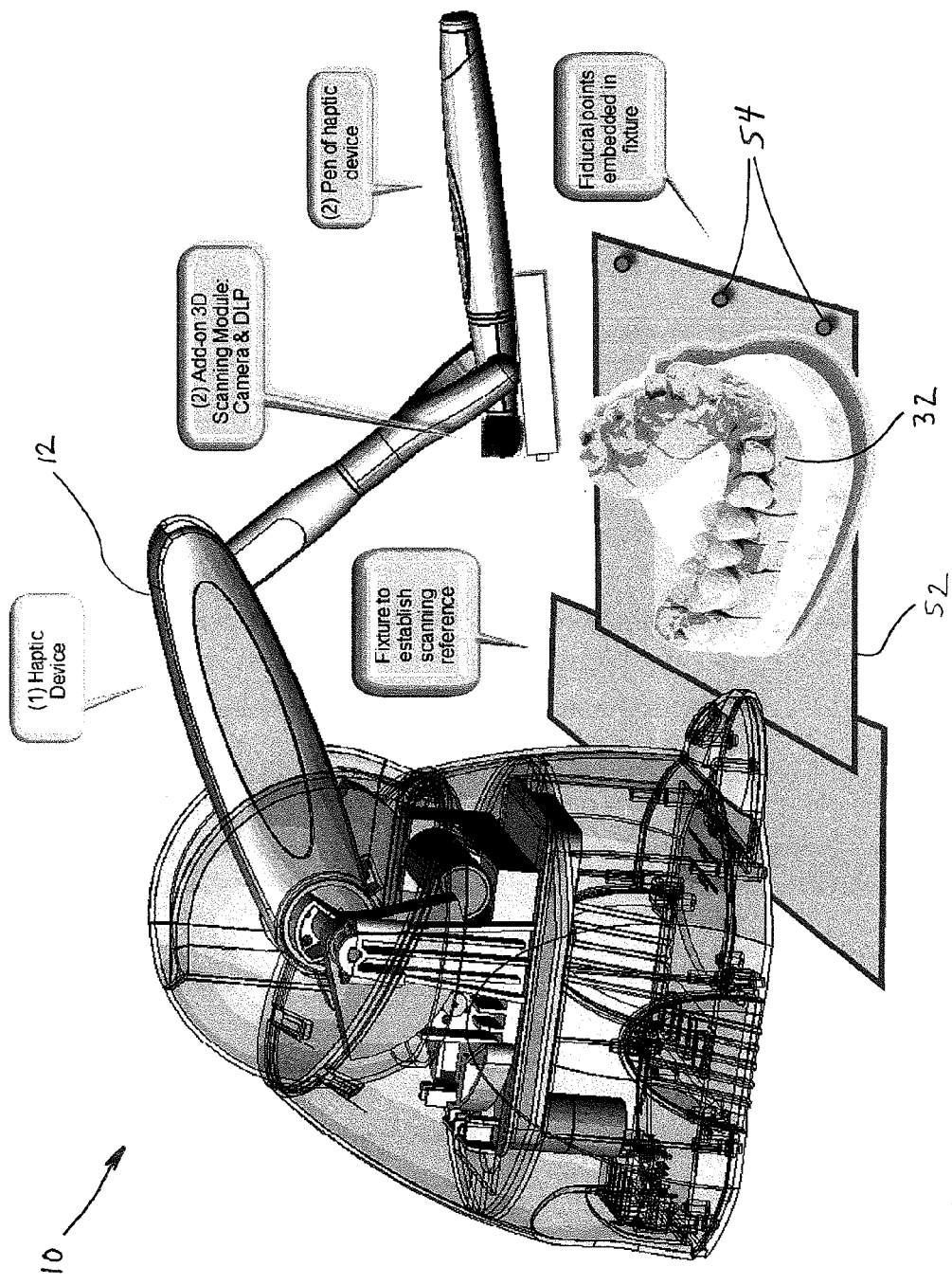
FIG. 4 is a schematic perspective view of a haptically guided scanning system that includes an integrated fixture with embedded fiducial points that establish a scanning reference, according to an illustrative embodiment of the invention.

As depicted in FIG. 4, when scanning three-dimensional objects, it may be useful to include a fixture or integrated extension 52 with known landmark or fiducial points 54 in order to provide ground truth information about the geometry of the three-dimensional scene. These fiducial points 54 may be used to assist in aligning data between multiple acquisitions, or in correcting spatial distortions introduced in the Point Cloud construction step (step 44). Thus, in one embodiment, the haptically guided scanning system 10 is provided with an integrated extension 52 that includes fiducial points 54 so that a scanning reference frame may be calculated.

In addition to or instead of including fiducial points 54, the integrated extension 52 may include special markings geared towards calibrating the camera 21, such as a three-dimensional range camera. Because the reconstruction algorithms generally assume a known geometry or relationship between the camera 21 and structured-light projector 20, calibration to a known image is important.

Additionally, in some cases, the haptic device 12 may constrain the available viewpoints for scanning. For example, the kinematic structure of the haptic device 12, such as the PHANTOM® device, may include stops or joint limits. To scan the entire object 32, it may therefore be necessary to move, twist, or spin the object 32 during the scanning process. Referring again to FIG. 3, an additional twist or other movement may be corrected in an alignment step (step 48) with the appropriate mathematics. To facilitate this correction, the scanning system 10 may include a structure for providing a fixed amount of rotation (e.g., 90 degrees or 180 degrees) or direct measurement through a rotary position sensor, such as an encoder or potentiometer.

Figure 5:
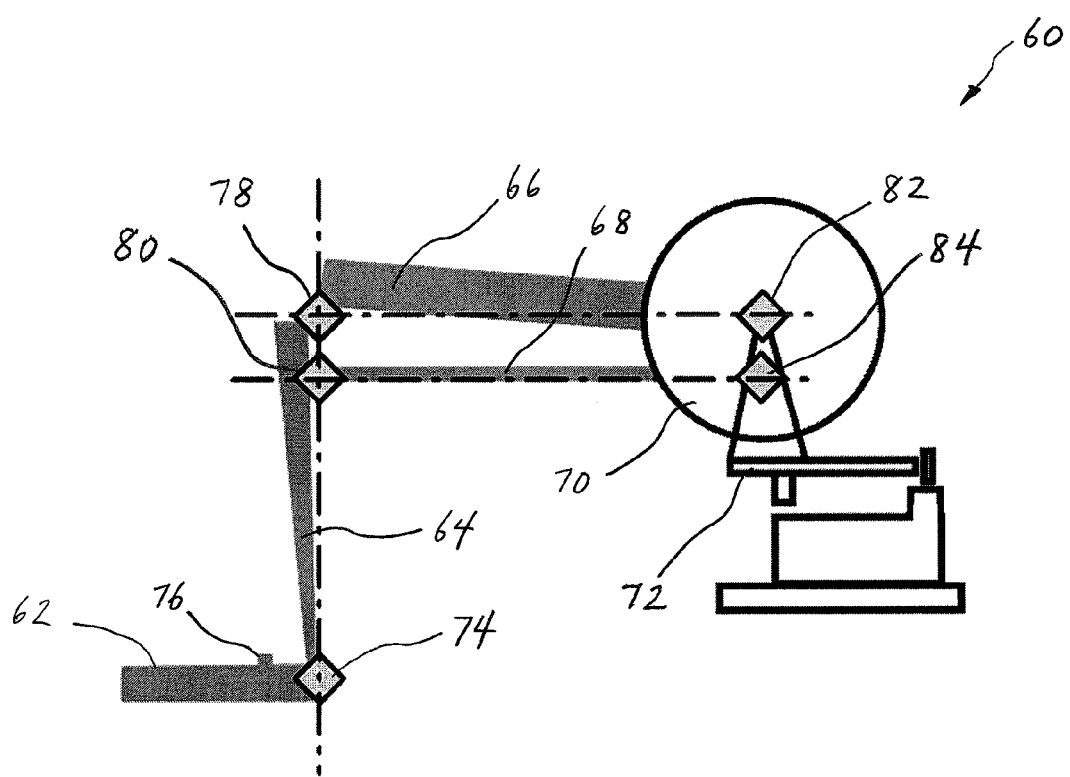
FIG. 5 is a schematic view of a haptic device, according to an illustrative embodiment of the invention.

Referring to FIG. 5, in certain embodiments, a haptic device 60 includes a user connection element or pen/stylus 62, a linkage 64, parallel linkages 66 and 68, a linkage disk 70, and a base disk 72. The pen 62 is attached to an end of linkage 64 at a pen joint 74. The pen 62 may include a switch 76, for example, to activate the haptic device 60 or initiate the scan of an object. An opposite end of the linkage 64 is attached to the two parallel linkages 66, 68 at linkage joints 78, 80. As depicted, the parallel linkages 66, 68 are connected to the linkage disk 70 at disk joints 82, 84. The linkage disk 70 may be attached to the base disk 72, which has a central axis that is perpendicular to a central axis of the linkage disk 70.

The position and orientation of the pen 62 in three-dimensional space is controlled with one or more actuators. For example, the haptic device 60 may include actuators to rotate the linkage disk 70 and/or the base disk 72. In addition, the disk joints 82, 84 may include one or more actuators to adjust the positions of one or both disk joints 82, 84 on the linkage disk 70. The linkage 64, parallel linkages 66, 68, linkage disk 70, base disk 72, and actuators are used to drive the pen 62 up, down, right, left, forwards, and/or backwards, as needed.

In certain embodiments, the pen 62 may be rotated about the pen joint 74 in one or more directions. For example, the pen 62 may be rotatable around a central axis of the pen 62. The pen joint 74 may also include a gimbal assembly to allow the pen 62 to be rotated about one or more axes that are perpendicular to the central axis of the pen 62. The pen joint 74 may include one or more actuators to control the orientation of the pen 62.

Figure 6:
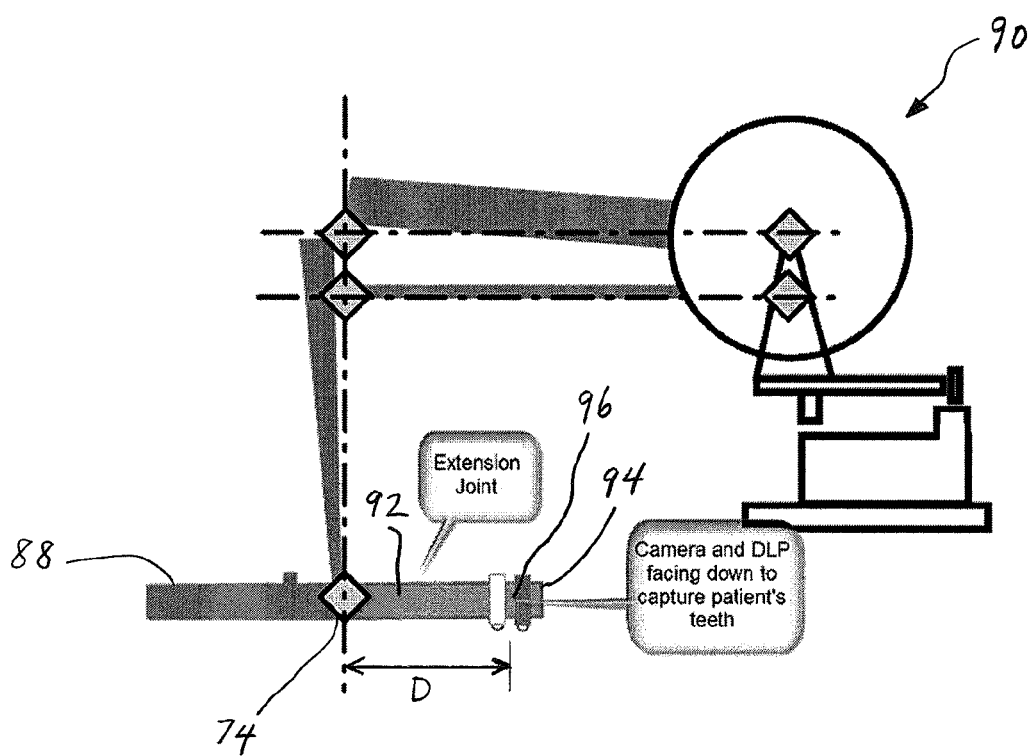
FIG. 6 is a schematic view of a haptic device that includes an extension joint and an add-on scanning module, according to an illustrative embodiment of the invention.

Referring to FIG. 6, to facilitate the scanning of objects that are difficult to reach or access, a pen 88 of a haptic device 90 includes an extension joint 92. The extension joint 92 extends from the pen joint 74 to a tip 94 where a scanning module 96 is located. As depicted, the scanning module 96 may include a camera and a DLP device. A length of the extension joint 92 may be fixed, or it may extendable. For example, the extension joint 92 may extend in the manner of a telescope. An actuator may be included to extend and/or retract the extension joint 92. In certain embodiments, a distance D between the scanning module 96 and the pen joint 74 may be between about 1 inch and about 12 inches, or between about 2 inches and about 4 inches. In one embodiment, the distance D is about 3 inches.

Each of the haptic devices described above and depicted in FIGS. 1 and 4-6 may be any suitable haptic device. For example, the haptic device may be any one of the following haptic devices manufactured by SensAble Technologies, Inc. of Wilmington, Mass.: a PHANTOM® Premium 1.5/6DOF or 1.5 High force/6DOF haptic device; a PHANTOM® Premium 1.0, 1.5, 1.5 High Force, or 3.0 haptic device; and a PHANTOM® Premium 3.0/6DOF haptic device. The haptic device may include various handles and/or end effectors.

In certain embodiments, the methods, systems, and apparatus described herein are configured for use in a Minimally Invasive Surgery (MIS) system. The system may be used to scan anatomical structures, such as a prostate gland, a gall bladder, a pancreas, a stomach, an appendix, a liver, and/or other organs or body parts. In one embodiment, the system enables a surgeon or other medical professional to view interior structures within a patient during evaluation, treatment, or surgery.

Examples of haptic devices that may be used with the system described herein include those described in the following U.S. patents, the disclosures of which are all incorporated herein by reference in their entireties: U.S. Pat. No. 5,898,599, titled, "Force Reflecting Haptic Interface," by Massie et al.; U.S. Pat. No. 6,671,651, titled, "3-D Selection and Manipulation with a Multiple Dimension Haptic Interface," by Goodwin, et al.; U.S. Pat. No. 6,985,133, titled, "Force Reflecting Haptic Interface," by Rodomista, et al.; U.S. Pat. No. 7,411,576, titled, "Force Reflecting Haptic Interface," by Massie, et al.

Examples of modeling systems and user interfaces (e.g., graphical and/or haptic interfaces) that may be used with the system described herein include those described in the following U.S. patents and patent applications, the texts of which are all incorporated herein by reference in their entireties: pending U.S. patent application Ser. No. 12/692,459, titled, "Haptically Enabled Coterminous Production of Prosthetics and Patient Preparations in Medical and Dental Applications," by Rawley et al., published as U.S. Patent Application Publication No. 2010/0291505; pending U.S. patent application Ser. No. 12/321,766, titled, "Haptically Enabled Dental Modeling System," by Steingart et al., published as U.S. Patent Application Publication No. 2009/0248184; pending U.S. patent application Ser. No. 11/998,457, titled, "Systems for Haptic Design of Dental Restorations," by Steingart et al., published as U.S. Patent Application Publication No. 2008/0261165; pending U.S. patent application Ser. No. 11/998,877, titled, "Systems for Hybrid Geometric/Volumetric Representation of 3D Objects," by Faken et al., published as U.S. Patent Application Publication No. 2008/0246761; U.S. Pat. No. 7,149,596, titled, "Apparatus and Methods for Modifying a Model of an Object to Enforce Compliance with a Manufacturing Constraint," by Berger et al.; U.S. Pat. No. 7,626,589, titled, "Haptic Graphical User Interface for Adjusting Mapped Texture," by Berger; U.S. Pat. No. 6,958,752, titled, "Systems and Methods for Three-Dimensional Modeling," by Jennings, Jr. et al.; U.S. Pat. No. 6,867,770, titled, "Systems and Methods for Voxel Warping," by Payne; U.S. Pat. No. 6,421,048, titled, "Systems and Methods for Interacting With Virtual Objects in A Haptic Virtual Reality Environment," by Shih et al.; U.S. Pat. No. 6,111,577, titled, "Method and Apparatus for Determining Forces to be Applied to a User Through a Haptic Interface," by Zilles et al.; U.S. Pat. No. 7,990,374, titled, "Apparatus and Methods for Haptic Rendering Using Data in a Graphics Pipeline," by Itkowitz; and pending U.S. patent application Ser. No. 11/169,271, titled, "Apparatus and Methods for Haptic Rendering Using a Haptic Camera View," by Itkowitz, published as U.S. Patent Application Publication No. 2006/0284834.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. Insofar as this is a provisional application, what is considered applicants' invention is not necessarily limited to embodiments that fall within the claims below.

What is claimed is:

1. A system for haptically enabled, three-dimensional scanning of a tangible object, the system comprising:
   a haptic interface device configured to provide haptic feedback to a user and receive input from the user during movement of an implement of the haptic interface device during three-dimensional scanning of a tangible object, wherein the implement comprises a camera;
   a graphical interface configured to provide graphical feedback to the user during three-dimensional scanning of the object; and
   a three-dimensional scanning application in communication with the haptic interface device and the graphical interface, wherein the scanning application, during scanning of the object:
   (a) obtains an image of the object captured by the camera upon activation of a user command;
   (b) determines, via a processor, a haptic guide at one or more positions and/or orientations in space in relation to the object from which further images are acquired and used for construction of a three-dimensional virtual representation of the object, wherein the haptic guide is determined using at least the image obtained in step (a);
   (c) delivers force to the user via the haptic interface device according to the haptic guide;
   (d) repeats one or more of steps (a) to (c) as additional images of the object are acquired; and
   (e) produces a three-dimensional virtual representation of the object using a subset of the acquired images, wherein the haptic guide is identified to facilitate further acquisition of images at the one or more positions and/or orientations in space in relation to the object to fill voids in the produced three-dimensional virtual representation, when used in combination with the previously obtained images.

2. The system of claim 1, wherein the implement of the haptic interface device comprises a stylus.

3. The system of claim 1, wherein activation of the user command occurs when the user presses a button of the haptic interface.

4. The system of claim 1, wherein the force is delivered to the user via the haptic interface device to constrain the movement of the implement by the user to positions and/or orientations corresponding to the haptic guide.

5. The system of claim 1, wherein the system is a part of a minimally invasive surgery (MIS) system.

6. The system of claim 1, wherein the force is delivered to the user, via the haptic interface device, to restrict or constrain the movement of the implement to provide a fixed camera focal length.

7. A method for haptically enabled, three-dimensional scanning of a tangible object, the method comprising:
(a) obtaining an image of the object upon activation of a user command, wherein the image is obtained, from a camera, during manipulation by the user of an implement of a haptic interface device about the object, wherein the implement comprises the camera;
(b) delivering graphical feedback to the user via a graphical display during the manipulation of the implement of the haptic interface device by the user;
(c) determining, via a processor, a haptic guide at one or more positions and/or orientations in space in relation to the object from which further images are acquired during the three dimensional scanning of the tangible object and used for construction of a three-dimensional virtual representation of the object, wherein the haptic guide is determined using at least the image obtained in step (a);
(d) delivering a force to the user via the haptic interface device according to the haptic guide;
(e) repeating one or more of steps (a) to (d) as additional images of the object are acquired; and
(f) producing a three-dimensional virtual representation of the object using a subset of the acquired images, wherein the haptic guide is identified to facilitate further acquisition of images at the one or more positions and/or orientations in space in relation to the object to fill voids in the produced three-dimensional virtual representation, when used in combination with the previously obtained images.

8. The method of claim 7, wherein the user command is activated by pressing a button of the haptic interface device.

9. The method of claim 7, wherein the implement of the haptic interface device comprises a stylus.

10. The method of claim 7, wherein delivering the force to the user via the haptic interface device comprises constraining the movement of the implement by the user to positions and/or orientations corresponding to the haptic guide.

11. The method of claim 7, wherein the object comprises at least one member selected from the group consisting of a tooth, a human face, a residual limb, an anatomical structure, and a mechanical part.

12. The method of claim 7, comprising the step of analyzing the three-dimensional virtual representation to reverse engineer the object.

13. The method of claim 7, wherein the force is delivered to the user, via the haptic interface device, to restrict or constrain the movement of the implement to provide a fixed camera focal length.

14. An apparatus for scanning a tangible object, comprising:
a user connection element;
a scanning module associated with the user connection element, the scanning module comprising a camera;
an actuator;
a linkage physically linking the user connection element to the actuator; and
a processor for determining force delivered to the user connection element by the actuator to restrict or guide movement of the user connection element according to a haptic guide, wherein the scanning module acquires a plurality of images of the object from the camera during the scan to produce a three-dimensional virtual representation, and wherein the haptic guide restricts or guides the movement of the user connection element to provide a fixed camera focal length using a subset of the plurality of images acquired of the object, wherein the haptic guide is identified to facilitate further acquisition of images at one or more positions and/or orientations in space in relation to the object to fill voids in the produced three-dimensional virtual representation, when used in combination with previously obtained images.

15. The apparatus of claim 14, wherein the user connection element comprises an extension joint for scanning a difficult to reach object.

16. The apparatus of claim 14, wherein the object comprises at least one member selected from the group consisting of a tooth, a human face, an anatomical structure, a residual limb, and a mechanical part.

17. The apparatus of claim 14, wherein the haptic guide facilitates movement of the user connection element by the user to one or more positions and/or orientations in space in relation to the object from which acquisition of images is employed for construction of a three-dimensional virtual representation of the object from the acquired images.

18. The apparatus of claim 14, wherein the haptic guide is updated, at least in part, according to one or more previously obtained images of the object.

19. The apparatus of claim 14, wherein the scanning module is a part of a minimally invasive surgery (MIS) system.

* * * * *